United States Patent
Melzer et al.

[11] Patent Number: 6,033,404
[45] Date of Patent: Mar. 7, 2000

[54] ENDOSCOPIC SURGICAL DEVICE

[75] Inventors: Andreas Melzer, Duisburg; Bernd Noesel, Luetjensee; Klaus Sczesny, Muehlenrade, all of Germany

[73] Assignee: Olympus Winter & Ibe GmbH, Hamburg, Germany

[21] Appl. No.: 09/112,422

[22] Filed: Jul. 9, 1998

[30] Foreign Application Priority Data

Jul. 10, 1997 [DE] Germany .......................... 197 29 459

[51] Int. Cl.[7] .................................................. A61B 17/36
[52] U.S. Cl. .................. 606/46; 606/41; 606/42
[58] Field of Search .................................. 600/104, 106; 606/37, 38, 39, 40, 41, 42, 45, 46, 49, 50

[56] References Cited

U.S. PATENT DOCUMENTS

| | | | |
|---|---|---|---|
| 4,430,996 | 2/1984 | Bonnet | 606/46 |
| 4,644,950 | 2/1987 | Valli | 606/46 |
| 5,347,992 | 9/1994 | Pearlman et al. | 600/131 |
| 5,431,645 | 7/1995 | Smith et al. | 600/106 |
| 5,469,841 | 11/1995 | Kobayashi et al. | 600/158 |

FOREIGN PATENT DOCUMENTS

| | | |
|---|---|---|
| 1 007 960 | 5/1957 | Germany . |
| 34 09 944 | 9/1985 | Germany . |
| 42 36 329 | 5/1994 | Germany . |
| 43 40 056 | 6/1995 | Germany . |
| 44 16 499 | 11/1995 | Germany . |

Primary Examiner—Linda C. M. Dvorak
Assistant Examiner—Brad C. Blaise
Attorney, Agent, or Firm—Walter C. Farley

[57] ABSTRACT

An endoscopic surgical device has a tubular shaft and an instrument carrier inside and moveable relative to the tubular shaft. A switch mechanism with which the device may be selectively switched into different operational states is coupled to movement of the instrument carrier.

3 Claims, 1 Drawing Sheet

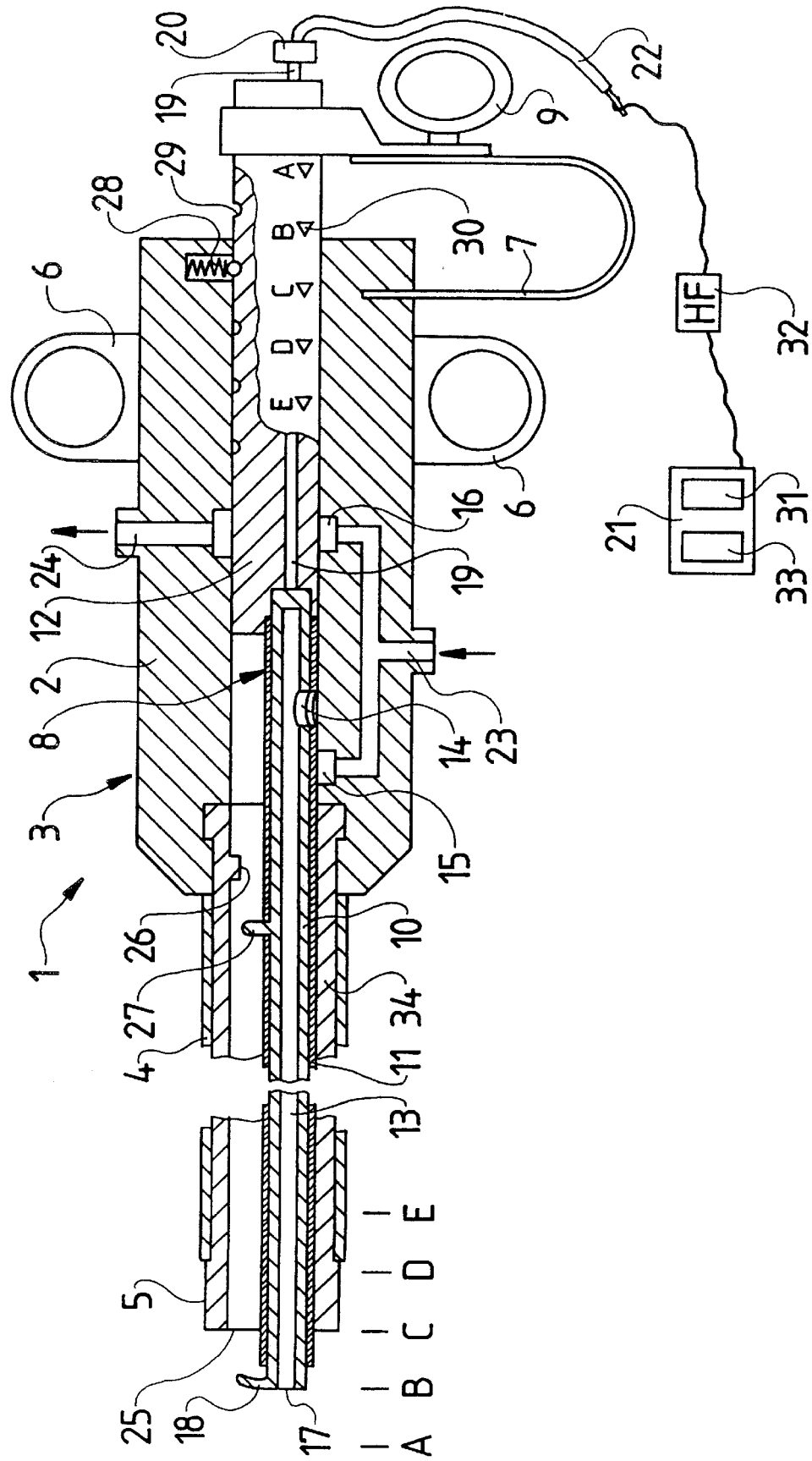

6,033,404

ENDOSCOPIC SURGICAL DEVICE

FIELD OF THE INVENTION

This invention relates to an endoscopic surgical device having a tubular shaft, a movable instrument carrier within the tubular shaft and a switch with which the device may be switched into different operating states.

BACKGROUND OF THE INVENTION

Devices of this type have a shaft portion and an instrument carrier. The shaft portion and instrument carrier are releasably connected together and movable relative to one another. They generally have switches for switching on different operational states. The important operational states are, e.g., the suction or flushing operation of a device. In the case of, e.g., electro-surgical devices there is also the current supply to cutting or coagulation electrodes which is also controlled by means of a switch.

The instrument carrier and switch are provided structurally isolated on devices of the type referred to above and consequently have their own handles for engagement by the operator. If, for instance, the handle is gripped by the operator for moving the instrument carrier and the operator subsequently wants to alter the operational state of the device, he must alter the position of his hand or fingers in order to change his grip over to the handle which moves the switch to alter the operational state. His grip must also be changed back again to the appropriate handle for the purpose of moving the instrument carrier again. These steps require a certain amount of practice and dexterity of the fingers.

Furthermore, the construction of devices of this type is relatively complex since a relatively large number of mechanical components are assembled. Maintenance, cleaning and disinfection of the devices are thus correspondingly difficult and costly.

SUMMARY OF THE INVENTION

An object of the invention to provide a device of the type referred to above which may be operated simply and is structurally simplified.

Briefly described, the invention comprises an endoscopic surgical instrument including a tubular shaft and an instrument carrier within the interior of and movable relative to the tubular shaft and including a switch with which the device may be switched into different operating states, the actuation of the switch being coupled to the movement of the instrument carrier.

Because in this device in accordance with the invention the actuation of the switch is coupled with the actuation of the instrument carrier, only one handle is necessary for the movement of the instrument carrier and for the actuation of the switch. Since both functions are performed with the same handle, there is no longer any need for one to change one's grip. Operation is thus substantially simplified. The constructional complexity is minimized and maintenance and cleaning or disinfection of the device may be performed more easily.

It would be theoretically possible to provide a control element which engages a separate switch and actuates it when the instrument carrier moves. Advantageously, however, associated members are provided on the instrument carrier and the tubular shaft, respectively, which constitute the switch. When the instrument carrier moves, these members move into engagement or are moved out of engagement and thus bring about the desired switching state.

A switch can have, e.g., a contact tongue which is located on the instrument carrier and which, when moved, engages a contact provided on the tubular shaft and constituting a further component of the switch, so that a circuit is then closed.

A further possibility for a switch is to provide bores at predetermined positions on the tubular shaft and on the instrument carrier, which bores move into alignment when the instrument carrier moves and make a flow of liquid possible, when in engagement.

In addition to the particularly simple operation and the particularly simple construction of the embodiment under discussion, there is a further advantage that when the instrument carrier is retracted out of the tubular shaft the switch is always open and cleaning is thus very simple.

Advantageously, a plurality of switches are provided on a device for effecting different operational states. As discussed above, these switches advantageously consist of associated members on the instrument carrier and on the tubular shaft which move into engagement in defined relative positions of the instrument carrier within the tubular shaft and then bring about the desired switching state.

A plurality of switching states, such as the application of electric current, suction and flushing flows and the like may be controlled in this manner. The universal applicability of the device may thus be extended as desired.

It would be possible to couple the actuation of the switch with radial movement of the instrument carrier. Rotating the instrument carrier whilst simultaneously maintaining unaltered the position of the tubular shaft may, however, only be performed with difficulty with one hand.

It is therefore advantageously provided in accordance with a further embodiment of the invention that the actuation of the switch is coupled with the axial movement for the use of a working instrument.

A further advantage of using the axial movement is that switches, which may be actuated by sliding movement, are very simple to manufacture.

Markings can also be provided which ensure exact recognition of the current switching position on the device, particularly when constructed with a plurality of switching functions.

BRIEF DESCRIPTION OF THE DRAWING

The invention is illustrated schematically by way of example in the drawing, which is a side elevation, in longitudinal section, of an instrument incorporating the invention.

DESCRIPTION OF THE PREFERRED EMBODIMENT

In the drawing, a device 1 is shown in section and includes a tubular shaft 3 comprising a main body 2 and a tube 34.

The main body 2 is of electrically non-conductive construction in this embodiment and is rigidly connected to the electrically conductive tube 34 whose outer surface is insulated with an electrically non-conductive layer 4. Formed at the distal end of the tube 34 is an un-insulated surface portion 5 which acts as a coagulation electrode. The main body 2 has two finger rings 6 and is connected by means of a spring 7 to the instrument carrier 8 which is thus mounted, restrained against rotation, in the main body 2 and the tube 34. The instrument carrier has a thumb ring 9 for its operation.

The instrument carrier 8 contains a tube member 10 towards the distal end of the carrier, tube 10 being electrically insulated from the interior of tube 34 by an electrical insulating layer 11. An electrically non-conductive guide member 12 is mounted at the proximal end of carrier 8. Tube member 10 has a flushing passage 13 with a side opening 14 which can be brought into registry with connections 15 and 16 in main body 2 in order to permit flushing liquid to flow to outlet 17 at the distal end. Instrument carrier 8 carries a cutting electrode 18 at the distal end of tube member 10. Cutting electrode 18 is electrically connected by a line 19 within the instrument carrier 8 to an HF connection 20 mounted proximally on guide member 12. The current flow via a line 22 from HF source 32 to HF connection 20 may be activated by actuating a foot switch 21.

Main body 2 has a flushing connection 23 which communicates with connections 15 and 16, and a vacuum connection 24, through which it is possible for liquid to be removed by suction through an opening 25 communicating with the distal end of tube 34 when the instrument carrier 8 is in the appropriate position in main body 2. Furthermore, electrical contacts 26 and 27, which are matched to one another, are provided respectively on the interior of tube 34 and on tube member 10 of instrument carrier 8. The axial position of instrument carrier 8 within main body 2 may be brought into any one of five positions in this embodiment by means of a spring-loaded locking device 28, which is movable into engagement with one of five grooves 29 in instrument carrier 8. These five positions correspond to the five possible operating states, identifying indicia of which may be read from markings 30 on guide member 12. Main body 2 is held by the user's index and middle finger with the aid of the finger rings 6 while the thumb within the thumb ring 9 on the instrument carrier can move the latter axially within the main body 2 and thus activates a selected one of the individual switch positions. The five possible axial positions of the instrument carrier are indicated in the drawing at the distal end of the device with the letters A, B, C, D and E.

Specifically, the letters identify the following operational states which are selectable by the above described switch means, including the electrical contacts as well as the conduit passages and openings:

A=Flushing

B=Cutting

C=Coagulation

D=Suction

E=Cleaning=Flushing and Suction

If the distal end of instrument carrier 8 is located in position A, flushing connection 15 and bore 14 are in registry and a flushing liquid flows through the flushing passage 13 to outlet 17.

If the illustrated position B is reached, all the connections are sealed. The HF current from source 32 can flow to cutting electrode 18 via a push button 31 on foot switch 21.

In position C, cutting electrode 18 is retracted into tube 34, the connections remain sealed and contacts 26 and 27 come into engagement. HF current for the purpose of coagulation may be applied to coagulation electrode 5 via contacts 26 and 27 by operating a push button 33 on foot switch 21.

Contacts 26 and 27 are moved out of engagement in position D and the coagulation electrode is thus dead. Vacuum connection 24 is opened to the interior of main body 2 and thus to tube 34 and suction is thus applied at the distal end of tube 34.

Finally, flushing connection 16 is brought into registry with bore 14 in position E and flushing liquid can flow through passage 13 to outlet 17. The vacuum connection 24 remains open at the same time to the interior of main body 2 and thus also to tube 34 and there is thus suction at the distal end of tube 34. A cleaning cycle is thus initiated.

The invention does of course also permit other embodiments. Thus e.g. the number and sequencing of the switch positions is variable. Also possible are switches situated externally on the tubular shaft which can be actuated e.g. by levers which are mounted on the instrument carrier and project outwardly to the switches.

The switching functions can also be achieved by means of rotation of the instrument carrier within the tubular shaft. With appropriate construction of the device; a combination of rotational movement and axial displacement would also be possible.

The switches can be arranged both proximally and distally so that e.g. a switch state can be achieved by the cutting electrode of the illustrated embodiment projecting into the tubular shaft and coming into contact with it so that the flow of current is made possible, e.g. to the coagulation electrode at the distal end of the tubular shaft.

What is claimed is:

1. An endoscopic surgical instrument comprising a tubular shaft having an interior;

an instrument carrier within and movable relative to said interior of said tubular shaft;

switch means for selectively switching said instrument into one of a plurality of operating states; said switch means including pairs of members (26, 27; 14, 15; 14, 16; 12, 24) movable relative to each other, one of a pair being on said tubular shaft (3) and the other on said instrument carrier (8), and actuation means coupling said switch means (26, 27; 14, 15; 14, 16; 12, 24) to movement of said instrument carrier (8).

2. An endoscopic surgical instrument comprising a tubular shaft having an interior;

an instrument carrier within and movable relative to said interior of said tubular shaft;

switch means comprising a plurality of switches (26, 27;14, 15; 14, 16; 12, 24) for selectively switching said instrument into one of a plurality of operating states; and actuation means coupling said switch means (26. 27; 14, 15; 14, 16; 12, 24) to movement of said instrument carrier (8).

3. An endoscopic surgical instrument comprising a tubular shaft having an interior;

an instrument carrier within and movable relative to said interior of said tubular shaft;

switch means for selectively switching said instrument into one of a plurality of operating states;

actuation means coupling said switch means (26, 27; 14, 15; 14, 16; 12, 24) to movement of said instrument carrier (8), and indicia on said tubular shaft (3) and on said instrument carrier (8) identifying said operating state of the instrument.

* * * * *